United States Patent [19]

Angello et al.

[11] Patent Number: 4,824,660

[45] Date of Patent: Apr. 25, 1989

[54] METHOD OF DETERMINING THE VIABILITY OF TISSUE IN AN ORGANISM

[75] Inventors: Debra A. Angello, Charlottesville, Va.; Richard A. Wilson, Lake Oswego, Oreg.

[73] Assignee: Paul S. Angello, Lake Oswego, Oreg.; a part interest

[21] Appl. No.: 741,805

[22] Filed: Jun. 6, 1985

[51] Int. Cl.[4] ..................... A61K 49/02; A61K 49/00
[52] U.S. Cl. ........................................... 424/1.1; 424/9
[58] Field of Search ..................................... 424/1.1, 9

[56] References Cited

U.S. PATENT DOCUMENTS 4,364,922 12/1982 Berne et al. .............................. 424/9

OTHER PUBLICATIONS

Knapp et al., J. Nuclear Medicine, 25(9), pp. 989–997 (1984).
Melin, Jacques A. et al., "Differences in Thallium-201 Uptake in Reperfused and Nonreperfused Myocardial Infarction," Circulation Research, vol. 53, No. 3, Sep. 1983, pp. 414–419.
Braunwald, Eugene et al., "The Stunned Myocardium: Prolonged Post-Ischemic Ventricular Dysfunction," Circulation, vol. 66, No. 2, Dec. 1982, pp. 1146–1149.
Pohost, Gerald M. et al., "Thallium Redistribution: Mechanisms and Clinical Utility," Seminars in Nuclear Medicine, vol. X, No. 1, Jan. 1980, pp. 70–93.
Liu, Peter et al., "Normalization of Persistent Defects on Thallium Scans after Myocardial Revascularization: Scar or Ischemia?", Journal of American College of Cardiology, vol. 3, No. 2, Feb. 1984, p. 607.
Zimmer, H.-G., "Effects of Inosine on Cardiac Adenine Nucleotide Metabolism in Rats," Advances in Myocardiology, vol. 6, 1985, pp. 173–183.
Angello, Debra A. et al., "The Effect of Eating on Thallium-201 Myocardial Redistribution Post Ischemia," Report Under Medical Research Foundation and NRSA Grant, F32-HC07135-01 From the National Institutes of Health, Bethesda, Md.
Angello, Debra A. et al., "Effect of Ribose on Postischemic Thallium-201 Kinetics," Report Under NRSA grant F32-HL07135-01 from the National Institutes of Health, Bethesda, Md., and the American Heart Association, Oregon Affiliate.
Strauss, H. William et al., "Thalium-201 for Myocardial Imaging-Relation of Thallium-201 to Regional Myocardial Perfusion," Circulation, vol. 51, Apr. 1975, pp. 641–645.
Carlin, Ronald D. and Jan, Kung-Ming, "Mechanism of Thallium Extraction in Pump Perfused Canine Hearts," The Journal of Nuclear Medicine, vol. 26, No. 2, Feb. 1985, pp. 165–169.
Gehring, P. J. and Hammond, P. B., "The Interrelationship Between Thallium and Potassium in Animals," The Journal of Pharmacology and Experimental Therapeutics, vol. 155, No. 1, Jan. 1967, pp. 187–201.

(List continued on next page.)

Primary Examiner—John F. Terapane
Assistant Examiner—J. E. Thomas
Attorney, Agent, or Firm—Stoel Rives Boley Jones & Grey

[57] ABSTRACT

A method of determining the viability of tissue in a region of an organism comprises the steps of introducing an ATP repleting agent into the region and monitoring the region to determine its effect on T1-201 distribution in the region. The capability of viable tissue to synthesize ATP and increase its ATP stores provides an indication of the viability of the tissue in the region. In a preferred embodiment of the method, ribose, which is a high energy phosphate precursor and an ATP repleting agent, is introduced into heart tissue that is being monitored by T1-201 scintigraphy. The ribose increases the rate and extent of T1-201 distribution in the heart tissue, thereby allowing the determination of viable "stunned" heart tissue. That viable tissue is distinguishable from nonviable tissue is attributed to the capability of the former to synthesize ATP and increase its ATP stores in response to the administration of the ATP repleting agent. Such manipulation of ATP stores in a region of tissue effects a detectable change in T1-201 distribution in that region. The method permits, therefore, the rapid determination of viable heart tissue. R 25 Claims, 1 Drawing Sheet Weiss, Edward S. et al., "Evaluation of Myocardial Metabolism and Perfusion with Positron-Emitting Radionuclides," *Progress in Cardiovascular Diseases*, vol. XX, No. 3, Nov./Dec. 1977, pp. 191-206.

Bergmann, Steven R. et al. "The Dependence of Accumulation of $NH_3$ by Myocardium on Metabolic Factors and Its Implications for Quantitative Assessment of Perfusion," *Circulation*, vol. 61, No. 1, Jan. 1980, pp. 34-43.

L'Abbate, A. et al., "Myocardial Kinetics of Thallium and Potassium in Man," *Circulation*, vol. 60, No. 4, Oct. 1979, pp. 776-785.

Mullani, Nizar A. et al., "Myocardial Perfusion with Rubidium-82.1, Measurement of Extraction Fraction and Flow with External Detectors," *The Journal of Nuclear Medicine*, vol. 24, Oct. 1983, pp. 898-906.

Selwyn, Andrew P. et al., "Relation Between Regional Myocardial Uptake of Rubidium-82 and Perfusion: Absolute Reduction of Cation Uptake in Ischemia," *The American Journal of Cardiology*, vol. 50, Jul. 1982, pp. 112-121.

Wilson, Richard A. et al., "Rubidium-82 Myocardial Uptake and Extraction after Transient Ischemia: PET Characteristics," *Journal of Computer Assisted Tomography*, vol. 11, Jan./Feb. 1987, pp. 60-66.

Kline, Robert C. et al., "Myocardial Imaging in Man with 1-123 Meta-Iodobenzylguanidine," *The Journal of Nuclear Medicine*, vol. 22, No. 2, Feb. 1981, pp. 129-132.

Holman, B. Leonard, and Sia, S. T. Benjamin, "Cardiac Scintigraphy with Technetrium Isonitriles," *Cardio Imaging*, May 1987, pp. 34-38, 77.

Deutsch, Edward et al., "Cationic Tc-99m Complexes as Potential Myocardial Imaging Agents," *The Journal of Nuclear Medicine*, vol. 22, No. 10, Oct. 1981, pp. 897-907.

Holman, B. Leonard et al., "A New TC-99m Labeled Myocardial Imaging Agent, Hexakis (t-Butylisonitrile)-Technetrium (1) [Tc-99m TB1]: Initial Experience in the Human," *The Journal of Nuclear Medicine*, vol. 25, Dec. 1984, pp. 1350-1355.

Zimmer, H.-G. et al., "Ribose Intervention in the Cardiac Pentose Phosphate Pathway is not Species-Specific," *Science*, vol. 223, Feb. 1984, pp. 712-714.

Zimmer, H.-G. et al., "De Novo Synthesis of Myocardial Adenine Nucleotides in the Rat," *Circulation Research*, vol. XXXII, May 1973, pp. 635-642.

Lazer, Harold L., "Myocardial Energy Replenishment and Reversal of Ischemic Damage by Substrate Enhancement of Secondary Blood Cardioplegia with Amino Acids during Reperfusion," *The Journal of Thoracic and Cardiovascular Surgery*, vol. 80, No. 3, Sep. 1980, pp. 350-359.

Harmsen, Eef et al., "Enhanced ATP and GTP Synthesis from Hypooxanthine or Inosine after Myocardial Ischemia," pp. H37-H43.

Marshall, Robert C. et al., "Identification and Differentiation of Resting Myocardial Ischemia and Infarction in Man with Positron Computed Tomography, $^{18}F$-labeled Fluorodeoxyglucose and N-13 Ammonia," *Circulation*, vol. 67, No. 4, Apr. 1983, pp. 766-778.

Gibson, Robert S., et al., "Prospective Assessment of Regional Myocardial Perfusion Before and After Coronary Revascularization Surgery by Quantitative Thallium-201 Scintigraphy," *Journal of American College of Cardiology*, vol. 1, No. 3, Mar. 1983, pp. 804-815.

Wynne, Joshua and Holman, Leonard, "Acute Myocardial Infarct Scintigraphy with Infarct-Avid Radiotracers," *The Medical Clinics of North America*, vol. 64, No. 1, Jan. 1980, pp. 119-144.

Ellis, Stephen G. et al., "Response of Reperfusion-salvages, Stunned Myocardium to Inotropic Stimulation," *American Heart Journal*, vol. 107, No. 1, Jan. 1984, pp. 13-19.

Maurer, Gerald and Nanda, Navin C., "Two Dimensional Echocardiographic Evaluation of Exercise- Induced Left and Right Ventricular Asynergy: Correlation with Thallium Scanning," *The American Journal of Cardiology*, vol. 48, Oct. 1981, pp. 720-727.

Bodenheimer, Monty M. et al., "Relationship Between Regional Myocardial Perfusion and the Presence, severity and Reversibility of Asynergy in Patients with Coronary Heart Disease," *Circulation*, vol. 58, No. 5, Nov. 1978, pp. 789-795.

Popio, Kenneth A. et al., "Post-Extrasystolic Potentiation as a Predictor of Potential Myocardial Viability: Preoperative Analyses Compared with Studies after Coronary Bypass Surgery," *The American Journal of Cardiology*, vol. 39, Jun. 1977, pp. 944-953.

Zimmer, H.-G. et al., "Stimulation of Myocardial Adenine Nucleotide Biosynthesis by Pentoses and Pentitols," *European Journal of Physiology*, vol. 376, 1978, pp. 223-227.

(List continued on next page.)

Zimmer, H.-G., "Restitution of Myocardial Adenine Nucleotides: Acceleration by Administration of Ribose," *Journal de Physiologie*, vol. 76, No. 7, Jul. 1980, pp. 769–775.

Pasque, Michael K. et al., "Ribose-Enhanced Myocardial Recovery Following Ischemia in the Isolated Working Rat Heart," *The Journal of Thoracid and Cardiovascular Surgery*, vol. 83, No. 3, Mar. 1982, pp. 380–398.

Siess, M. et al., "Cardiac Synthesis and Degradation of Pyridine Nucleotides and the Level of Energy-Rich Phosphates Influenced by Various Precursors," *Advances in Myocardiology*, vol. 4, 1983, pp. 287–308.

Wilson, Richard A. et al., "Effect of Glucose-Insulin-Potassium Infusion on Thallium Myocardial Clearance," *Laboratory Investigation–Nuclear Cardiology*, vol. 68, No. 1, Jul. 1983, pp. 203–209.

Okada, Robert D., "Kinetics of Thallium-201 in Reperfused Canine Myocardian after Coronary Artery Occlustion," *J.A.C.C.*, vol. 3, No. 5, May 1984, pp. 1245–1251.

Okada, Robert D. et al., "The Use of Preintervention and Postintervention Thallium Imaging for Assessing the Early and Late Effects of Experimental Coronary Arterial Reperfusion in Dogs," *Laboratory Investigation–Nuclear Cardiology*, vol. 69, No. 6, Jun. 1984, pp. 1153–1160.

Haas, Gary S. et al., "Reduction of Postischemic Myocardial Dysfunction by Substrate Repletion during Reperfusion," *Myocardial Protection*, vol. 70, Supp. I, Sep. 1984, pp. 1–65.

Wilson, Richard A. et al., "The Effect of Glucose-Insulin-Potassium on Thallium-201 Myocardial Redistribution," *Int. J. Nucl. Med. Biol.*, vol. 12, No. 2, 1985, pp. 97–101.

Mauser, M. et al., "Influence of Ribose, Adenosine, and AICAR on the Rate of Myocardial Adenosine Triphosphate Synthesis during Reperfusion after Coronary Artery Occlusion in the Dog," *Circulation Research*, vol. 56, No. 2, Feb. 1985, pp. 220–230.

Liu, Peter et al., "The Persistent Defect on Exercise Thallium Imaging and its Fate after Myocardial Revascularization: Does it Represent Scar or Ischemia?," *American Heart Journal*, vol. 110, No. 5, Nov. 1985, pp. 996–1001.

Wilson, Richard A. et al., "The Effect of Eating on Thallium Myocardial Imaging," *Chest*, vol. 89, No. 2, Feb. 1986, pp. 195–198.

Pohost, G. M. et al., "Positron Emission Tomography for the Evaluation of Regional Myocardial Blood Flow," *New Concepts in Cardiac Imaging*, 1987, p. 199.

Pohost, G. M. et al., "Differentiation of Transiently Ischemic from Infarcted Myocardium by Serial Imaging after a Single Dose of Thallium-201," *Circulation*, vol. 55, No. 2, Feb. 1977, pp. 294–302.

McAnulty, John H., "Improvement in Left Ventricular Wall Motion Following Nitroglycerin," *Circulation*, vol. 51, Jan. 1975, pp. 140–145.

See, Jackie R., "Significance of Reduced Regional Myocardial Blood Flow in Asynergic Areas Evaluated with Intervention Ventriculography," *The American Journal of Cardiology*, vol. 43, Feb. 1979, pp. 179–185.

Higginbotham, Michael B., "Mechanism and Significance of a Decrease in Ejection Fraction During Exercise in Patients with Coronary Artery Disease and Left Ventricular Dysfunction at Rest," *JACC*, vol. 3, No. 1, Jan. 1984, pp. 88–97.

Wann, L. Samuel et al., "Exercise Cross-Sectional Echocardiography in Ischemic Heart Disease," *Circulation*, vol. 60, No. 6, Dec. 1979, pp. 1300–1308.

Wackers, Frans J. Th., "Characteristics of Radiopharmaceuticals in Nuclear Cardiology, Implications for Practical Cardia Imaging," *Nuclear Imaging, in Clinical Cardiology*, 1984, pp. 19–20.

Wilson, Richard, "Myocardial Blood-Flow: Clinical Application and Recent Advances," Nuclear *Imaging in Clinical Cardiology*, 1984, pp. 39–54.

Zimmer, H.-G., "Normalization of Depressed Heat Function in Rats by Ribose," *Science*, vol. 220, Apr. 1983, pp. 81–82.

Angello, Debra A. et al., "Acceleration of Thallium-201 Redistribution Post Ischemia by Ribose," *Circulation*, vol. 74(II), Nov. 1986, p. II-60.

Angello, Debra A. et al., "Effects of Ribose on Post Ischemic Thallium-201 Kinetics," *The Journal of the American College of Cardiology*, vol. 9, No. 2, Mar. 1987, p. 25A.

Angello, Debra A. et al., "Ribose Improves Postischemic Myocardial Function and Thallium-201 Redistribution," to be published in *Circulation*, Nov. 1987.

METHOD OF DETERMINING THE VIABILITY OF TISSUE IN AN ORGANISM

BACKGROUND OF THE INVENTION

The present invention relates to methods of detecting viable tissue in an organism, and in particular, to such a method that relies upon the capability of viable tissue to utilize an adenosine triphosphate (ATP) repleting agent to synthesize ATP.

There exist specific techniques for determining the viability of biological tissues of different types in an organism. For example, thallium-201 (Tl-201) scintigraphy has been used extensively in the diagnosis of coronary artery disease. Tl-201 scintigraphy is the process of introducing Tl-201 into heart tissue, scanning the heart to detect the radioactive emissions induced by the Tl-201, and using the detected emissions to form images of the heart. A Tl-201 scan image identifies two types of defects, a "persistent defect" and a "transient defect." A persistent defect is defined as a region of heart tissue or myocardium that is deficient Tl-201 activity, and a transient defect is defined as a region of myocardium that is only temporarily deficient of Tl-201 activity.

Tl-201 scintigraphy is typically conducted in two separate studies in conjunction with exercise testing of a patient. Tl-201 is administered by injection into the patient's bloodstream. Tl-201 is administered during the first study at peak exercise during which single images of the heart are obtained in each of several projections. Whenever the images indicate generally uniform Tl-201 activity in all regions of the heart, the heart is considered to be free from defects. Whenever an image indicates a region of no or decrease Tl-201 activity, the heart is considered to have a defect. After a standard redistribution period of about four hours, imaging of the heart is repeated in similar projections. The defect regions of the first scan image are examined to determine whether the defect region "filled-in" with Tl-201 after the redistribution period between the first and second studies. A region that does not fill in with Tl-201 is denominated a persistent defect, which is currently viewed as representing scarred nonviable heart tissue. A region that does fill in with Tl-201 is denominated a transient defect, which is currently viewed as transiently ischemic but viable heart tissue that is "at risk" for infarction.

The interpretation of images developed by Tl-201 scintigraphy has been widely discussed by medical practitioners and researchers. For example, an article by Pohost, Gerald M. et al., "Thallium Redistribution: Mechanisms and Clinial Utility," *Seminars in Nuclear Medicine*, Vol. X, No. 1, January 1980, pp. 70–93, states that the uptake of Tl-201 is related to regional perfusion of viable heart tissue cells and the capability of the cells to extract the isotope. Pohost et al. conclude that periods of interrupted blood flow to regions of the heart (1) do not irreversibly affect the capability of reversibly damaged heart tissue cells in those regions to extract Tl-201, and (2) leads to a low extraction capability in those regions of irreversibly damaged heart tissue cells. In short, the Pohost et al. article suggests that Tl-201 imaging is clinically useful for distinguishing among noninschemic, ischemic but viable, and permanently injured heart tissue.

The clinical utility of Tl-201 myocardial imaging as advocated by Pohost et al. has, however, been challenged. For example, the abstract by Liu, Peter et al., "Normalization of Persistent Defects on Thallium Scans after Myocardial Revascularization: Scar or Ischemia?", *Journal of American College of Cardiology*, Vol. 3, No. 2, February 1984, p. 607, reports that a normalization of persistent Tl-201 image defects can occur after angioplasty of severely constricted coronary vessels. (Angioplasty is a "salvage" procedure by which a constriction in a blood vessel is at least partly dilated to increase the flow of blood through it.) Liu et al. recommend that persistent defects should no longer preclude reperfusion procedures in regions where the heart tissue was thought to be irreversibly injured.

In addition, the article by Melin, Jacques A. et al., "Differences in Thallium-201 Uptake in Reperfused and Non reperfused Myocardial Infarction," *Circulation Research*, Vol. 53, No. 3, September 1983, pp. 414–419, casts doubt on the validity of the assertion that Tl-201 is extracted or taken up only in viable tissue. Melin et al. report that, although there is a close correlation between Tl-201 uptake and regional myocardial blood flow, Tl-201 uptake occurs in reperfused infarcted tissue despite the necrosis thereof. The Tl-201 uptake occurring in reperfused infarcted tissue does so, however, in reduced concentrations relative to blood flow. Melin et al. conclude that their study demonstrates that the presence of Tl-201 uptake is an unreliable indicator of myocardial injury and that reperfused necrotic tissue may have remarkably high levels of Tl-201 uptake.

The article by Braunwald, Eugene et al., "The Stunned Myocardium: Prolonged Post-Ischemic Ventricular Dysfunction," *Circulation*, Vol. 66, No. 2, December 1982, pp. 1146–1149, proposes that ischemia, i.e., the temporary lack of blood supply to a tissue, is not an "all-or-none" process because recovery of mechanical function, biochemical or metabolic processes, and ultrastructural integrity in viable postischemic myocardial tissue may occur over prolonged periods, which can range from several hours to days. Braunwald et al. suggest that Tl-201 may redistribute very slowly into "sick" or "stunned" tissue from a lack of blood supply to the region. The article by Braunwald et al. suggests that there exists a need to distinguish "stunned" myocardium from permanently injured myocardium in interpreting a Tl-201 persistent defect image.

SUMMARY OF THE INVENTION

An object of the present invention is, therefore, to provide a reliable method of determining the viability of tissue in an organism.

Another object of this invention is to provide such a method that uses Tl-201 imaging to determine the viability of heart tissue.

A further object of this invention is to provide such a method that distinguishes nonviable heart tissue from "stunned" heart tissue in patients with persistent or resting defects.

Still another object of this invention is to provide such a method in which intervention with an ATP repleting agent is a vehicle for accelerating Tl-201 redistribution, and thereby hastening an accurate determination of the viability of the heart tissue.

The present invention is a method of determining the viability of tissue in a region of an organism. The method comprises the steps of introducing an ATP repleting agent into the region, introducing a blood flow marking medium into the circulatory system that supplies blood to the region, and determining the amount of marking medium appearing in the region in response to the presence of the ATP repleting agent. The ATP repleting agent and blood flow marking medium may be introduced in reverse order to that recited above. ATP is a substance normally found in living tissues and is used herein as an indicator of myocardial energy stores. This capability to synthesize ATP provides, therefore, an indication of the viability of the tissue in the region.

In a preferred embodiment of the invention, ribose, which is a high energy phosphate precursor and an ATP repleting agent, is intravenously introduced into the circulatory system of a patient. Tl-201 serves as the blood flow marking medium, which is injected into the circulatory system. The activity of Tl-201, in the heart tissue is measured as a function of time by a gamma camera to provide an indication of the viability of the heart tissue. The inventors' present theory is that the amount of Tl-201 extracted by the heart may be directly related to the integrity of the sodium-potassium ATPase active transport system by which Tl-201 is transported into the cell. Tl-201 is a monovalent cation and potassium analog. It is known that the cell membrane handles Tl-201 in a manner similar to potassium. This membrane transport system requires the presence of ATP for its normal function.

The intravenously injected ribose flows into the heart tissue to increase the rate and extent of Tl-201 distribution. The inventors' present theory is that the ribose repletes ATP stores which otherwise may remain at decreased levels in stunned myocardium for prolonged periods. The use of the ATP repleting agent alters Tl-201 redistribution and thereby facilitates the correct interpretation by Tl-201 scan images by eliminating the ambiguities inherent in such images in which persistent defects appear. In short, the use of an ATP stores promotes the recovery of stunned but viable heart tissue and the ability to use Tl-201 scintigraphy in the analysis for correctly determining the viability of the heart tissue.

Additional objects and advantages of the present invention will be apparent from the following detailed description of a preferred embodiment thereof, which proceeds with reference to the accompanying drawing.

DETAILED DESCRIPTION OF PREFERRED EMBODIMENT

Figure 1:
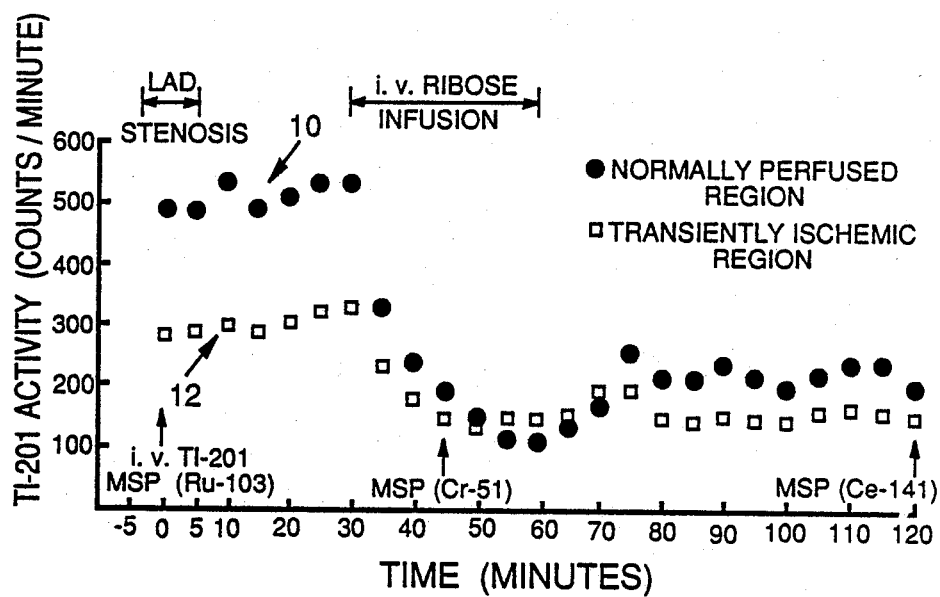
FIG. 1 is a graph that compares the rate and extent of normalization of Tl-201 activity in a transiently ischemic region and a normally perfused control region of the heart when ribose is intravenously infused into the circulatory system in accordance with the method of the present invention.

The preferred embodiment of the method is directed to the use of ribose as an ATP repleting agent that increases the rate and extent of Tl-201 redistribution in heart tissue.

The uptake of Tl-201 by the myocardium is defined as the product of myocardial blood flow and myocardial extraction of Tl-201. The exact mechanism by which the myocardial cell membrane extracts Tl-201 is not well understood. One of the premises underlying the method of the present invention is the normalization of ATP stores with ATP repleting agents, such as ribose, to restore normal processing of Tl-201 by the cell and thereby allow detection of cell viability by normalization of Tl-201 content within the cell.

The salutary effect of ribose in determining the existence of viable tissue was confirmed in an experiment that is set forth in the following example.

EXAMPLE

This example used the domestic swine, whose coronary anatomy is similar to that of human beings, to verify the method of the invention.

With reference to FIG. 1, the curve 10, which is comprised of dots, represents the Tl-201 activity of a normally perfused region of heart tissue; and the curve 12, which is comprised of squares, represents the Tl-201 activity in a transiently ischemic region of heart tissue. The transiently ischemic region of the heart tissue was created in the swine by a 10 minute stenosis, i.e., a critical interruption of blood flow, to about 25 percent of normal flow of the mid-left anterior descending coronary artery (LAD). Miniature cadmiumtelluride (CdTe) radiation detector probes were inserted in the transiently ischemic region and a normally perfused control region of the heart. The stenosis of the LAD artery is shown to have taken place from $-5$ minutes to $+5$ minutes on the time scale of FIG. 1. The time of intravenous Tl-201 injection (1.5mCi), which occurred midway through the stenosis period of the LAD artery, is represented as the 0 minute reference on the time scale. The 71-201 activity was measured as the average of five one-minute count intervals and is presented in units of counts-per-minute in FIG. 1.

Curves 10 and 12 show that the normally perfused region and the transiently ischemic region, respectively, are distinguishable by a Tl-201 activity difference of approximately 200 counts-per-minute for the first 30 minutes after injection of Tl-201. Intravenous ribose infusion (7mM at 2 ml/min) commenced 30 minutes after the introduction of Tl-201. The virtual elimination of the difference between Tl-201 activity after intravenous ribose infusion demonstrates the striking effect of the ribose on Tl-201 washout rates with more rapid redistribution in the post-ischemic period. The readings from the miniature CdTe radiation detector probes showed that the Tl-201 activity within both regions decreased marketdly with the intravenous ribose infusion for 30 minutes from the 30 minute to the 60 minute points of the experiment.

Curve 12 shows that Tl-201 activity within the transiently ischemic region rapidly normalized or redistributed relative to the Tl-201 activity within the normally perfused control region during the 30 minute ribose infusion. After the infusion was stopped, a difference in Tl-201 activity in normal and postischemic regions reappeared, but the difference was not so great as that during the first 30 minutes of the experiment.

The in-vivo relative measurements of Tl-201 activity by the two CdTe radiation detector probes were confirmed by in-vitro well counting of tissue from the two myocardial regions at the end of the study. Regional myocardial blood flow was measured by in-vitro counting of radiolabeled microspheres (MSP) of ruthenium-103 (Ru-103), chromium-51 (Cr-51), and cerium-141 (Ce-141) that were injected during the ten minute stenosis of the LAD, during intravenous ribose infusion at 45 minutes, and at the end of the 125 minute study, respectively.

The ratio of the regional LAD flow to the normally perfused circumflex coronary artery blood flow was 0.26 during moderate LAD stenosis, 0.82 during ribose infusion, and 0.74 at the end of the study. Regional wall motion in the transiently ischemic region measured as percentage systolic thickening increased by 10 percent from the period of inschemia to pre-ribose infusion and then increased by an additional 9 percent during ribose infusion. This improvement in mechanical function was sustained for an additional 30 minutes after the ribose infusion was stopped after 60 minutes into the study. The data from the study presented above demonstrate that ribose infusion actually accelerates the redistribution of Tl-201 content into transiently ischemic myocardium as administered in accordance with the method of invention.

The above-described experiment was repeated with the exception that saline was substituted for the ribose. The abrupt changes in regional Tl-201 activity were not observed with control animals infused with saline instead of ribose.

Although ribose, which is a pentose, was used as the ATP repleting agent in the above-described example, other ATP repleting agents may be used in the alternative. These include l-glutamate, l-aspartate, l-arginine, l-ornithine, and high energy phosphate precursors (such as inosine, hypoxanthine, adenosine, pentitols, and pentoses). In addition, rubidium-82 (RB-82) may be substituted for Tl-201 as the blood flow marking medium.

It will be obvious to those having skill in the art that many changes may be made in the above-described details of the preferred embodiment of the present invention. The scope of the invention without departing from the underlying principles thereof should, therefore, be determined only with reference to the following claims.

What is claimed is:

1. A method of determining the viability of a region of heart tissue, comprising:
   introducing a high energy phosphate precursor agent into the region of heart tissue;
   introducing a blood flow marking medium into the circulatory system that supplies blood to the region of heart tissue; and
   performing noninvasive myocardial imaging to monitor the amount of blood flow marking medium appearing in the region of heart tissue in response to the presence of the precursor agent, thereby to provide an indication of the viability of the region of heart tissue.

2. The method of claim 1 in which the precursor agent is selected from the group consisting essentially of pentoses, pentitols, adenosine, hypoxanthine, inosine, l-glutamate, l-aspartate, l-arginine, and l-ornithine.

3. The method of claim 1 in which the blood flow marking medium is Tl-201.

4. The method of claim 3 in which the amount of Tl-201 present in the region of heart tissue is monitored by:
   counting the number of radioactive emissions produced by the Tl-201; and
   correlating the number of measured emissions to the viability of the region of heart tissue.

5. The method of claim 1 in which the heart tissue is that of a human being.

6. A method of determining the viability of a region of heart tissue, comprising:
   introducing a ATP repleting agent into the region of heart tissue;
   introducing a blood flow marking medium into the circulatory system that supplies blood to the region of heart tissue; and
   performing noninvasive myocardial imaging to determine the amount of blood flow marking medium appearing in the region of heart tissue in response to the presence of the ATP repleting agent, thereby to provide an indication of the viability of the region of heart tissue.

7. The method of claim 6 in which the ATP repleting agent comprises a high energy phosphate precursor.

8. The method of claim 6 in which the ATP repleting agent is selected from the group consisting essentially of pentoses, pentitols, adenosine, hypoxanthine, inosine, l-glutamate, l-aspartate, l-arginine, and l-ornithine.

9. The method of claim 6 in which the blood flow marking medium is Tl-201.

10. The method of claim 1 in which the blood flow marking medium is Rb-82.

11. The method of claim 1 in which the heart tissue is that of a nonhuman animal.

12. The method of claim 3 in which the precursor agent is ribose.

13. The method of claim 6 in which the blood flow marking medium is Rb-82.

14. The method of claim 6 in which the heart tissue is that of a human body.

15. The method of claim 6 in which the heart tissue is that of a nonhuman animal.

16. The method of claim 7 in which the high energy phosphate precursor is ribose.

17. The method of claim 6 in which the ATP repleting agent is ribose.

18. The method of claim 9 in which the ATP repleting agent is ribose.

19. The method of determining the viability of a region of heart tissue, comprising:
   introducing a quantity of ribose into the region of heart tissue;
   introducing a blood flow marking medium into the circulatory system that supplies blood to the region of heart tissue; and
   monitoring the amount of blood flow marking medium appearing in the region of heart tissue in response to the presence of the ribose, thereby to provide an indication of the viability of the region of heart tissue.

20. The method of claim 19 in which the blood flow marking medium is Tl-201.

21. The method of claim 20 in which the amount of Tl-201 present in the region of the heart tissue is monitored by:
   counting the number of radioactive emissions produced by the Tl-201; and
   correlating the number of measured emissions to the viability of the region of heart tissue.

22. The method of claim 19 in which the blood flow marking medium is Rb-82.

23. The method of claim 19 in which the heart tissue is that of a nonhuman animal.

24. The method of claim 19 in which the heart tissue is that of a human being.

25. The method of claim 19 in which the amount of Tl-201 present in the region of heart tissue is monitored by performing noninvasive myocardial imaging.

* * * * *

UNITED STATES PATENT AND TRADEMARK OFFICE
CERTIFICATE OF CORRECTION

PATENT NO.     : 4,824,660  
DATED          : April 25, 1989  
INVENTOR(S)    : Debra A. Angello and Richard A. Wilson Page 1 of 1

It is certified that error appears in the above-identified patent and that said Letters Patent is hereby corrected as shown below:

<u>Title page,</u>
Item [57], ABSTRACT,
Line 21, (last line), delete "R".

<u>Column 1,</u>
Line 22, after "deficient" insert -- of --
Line 34, change "decrease" to -- decreased --.
Line 64, change "noninschemic" to -- nonischemic --.

<u>Column 3,</u>
Line 36, after "ATP" insert -- repleting agent to manipulate myocardial ATP --

<u>Column 4,</u>
Line 20, change "cadmiumtelluride" to -- cadmium-telluride --.
Line 29, change "71-201" to -- Tl-201 --.
Line 45, change "marketdly" to -- markedly --.

<u>Column 5,</u>
Line 5, change "inschemia" to -- ischemia --.

Signed and Sealed this

Thirteenth Day of May, 2003

JAMES E. ROGAN
*Director of the United States Patent and Trademark Office*